United States Patent
Mcerlean et al.

(10) Patent No.: US 11,083,521 B2
(45) Date of Patent: Aug. 10, 2021

(54) INTERFERENCE SUPPRESSION APPARATUS AND METHOD

(71) Applicant: EMBLATION LIMITED, Alloa (GB)

(72) Inventors: Eamon Mcerlean, Alloa (GB); Gary Beale, Alloa (GB)

(73) Assignee: EMBLATION LIMITED, Alloa (GB)

( * ) Notice: Subject to any disclaimer, the term of this patent is extended or adjusted under 35 U.S.C. 154(b) by 677 days.

(21) Appl. No.: 15/251,113

(22) Filed: Aug. 30, 2016

(65) Prior Publication Data

US 2017/0056106 A1    Mar. 2, 2017

(30) Foreign Application Priority Data

Aug. 31, 2015    (GB) .................................... 1515426

(51) Int. Cl.
*A61B 18/00* (2006.01)
*A61B 18/18* (2006.01)

(52) U.S. Cl.
CPC ............... *A61B 18/1815* (2013.01); *A61B 2018/00059* (2013.01); *A61B 2018/00577* (2013.01); *A61B 2018/183* (2013.01); *A61B 2018/1823* (2013.01); *A61B 2018/1892* (2013.01); *A61B 2562/18* (2013.01)

(58) Field of Classification Search
CPC ...... A61B 18/1815; A61B 2018/00053; A61B 2018/00059; A61B 2018/1823; A61B 2562/18; A61B 2562/182; H01B 11/18
See application file for complete search history.

(56) References Cited

U.S. PATENT DOCUMENTS

| | | | |
|---|---|---|---|
| 4,517,975 A | | 5/1985 | Garito et al. |
| 4,914,717 A | | 4/1990 | Gibbon |
| 5,091,707 A | * | 2/1992 | Wollmerschauser .. H04B 15/02 333/12 |
| 5,507,791 A | | 4/1996 | Sit'ko |
| 5,649,973 A | | 7/1997 | Tierney et al. |
| 5,683,386 A | | 11/1997 | Ellman et al. |
| 5,879,379 A | | 3/1999 | Mason et al. |
| 5,993,480 A | | 11/1999 | Burrows |
| 6,047,216 A | | 4/2000 | Carl et al. |

(Continued)

FOREIGN PATENT DOCUMENTS

| | | |
|---|---|---|
| CN | 1277879 | 12/2000 |
| EP | 2485326 | 8/2012 |

(Continued)

OTHER PUBLICATIONS

Parker, Carole (Specifying a Ferrite for EMI Suppression. Conformity, Jun. 2008). (Year: 2008).*

(Continued)

*Primary Examiner* — Jaymi E Della
*Assistant Examiner* — Rachel A. Vierra
(74) *Attorney, Agent, or Firm* — Sheridan Ross P.C.

(57) ABSTRACT

A medical microwave delivery system comprises a microwave generator for providing microwave energy, wherein the microwave generator is electrically isolated from an electrical earth of the medical microwave delivery system, a coaxial cable configured to transfer microwave energy from the microwave generator, and a ferrite element configured to at least partially surround at least part of the coaxial cable.

20 Claims, 4 Drawing Sheets

(56) References Cited

U.S. PATENT DOCUMENTS

| | | | |
|---|---|---|---|
| 6,104,959 A | | 8/2000 | Spertell |
| 6,710,673 B1* | | 3/2004 | Jokerst .................. H01F 17/062 |
| | | | 333/12 |
| 7,052,283 B2* | | 5/2006 | Pixley .................... H01R 24/42 |
| | | | 336/92 |
| 7,211,411 B2 | | 5/2007 | Neefe et al. |
| 7,292,893 B2 | | 11/2007 | Hoenig et al. |
| 7,981,112 B1 | | 7/2011 | Neev |
| 9,498,284 B2 | | 11/2016 | McErlean et al. |
| 9,543,061 B2* | | 1/2017 | McErlean ............ H01R 13/005 |
| 9,662,510 B2 | | 5/2017 | Beale et al. |
| 2001/0050605 A1* | | 12/2001 | Sugiura ................. H01F 17/062 |
| | | | 336/92 |
| 2003/0012830 A1 | | 1/2003 | Small |
| 2003/0225441 A1 | | 12/2003 | Boynton et al. |
| 2005/0251231 A1 | | 11/2005 | Goldberg |
| 2006/0020312 A1 | | 1/2006 | Eggers et al. |
| 2006/0235286 A1 | | 10/2006 | Stone et al. |
| 2008/0149100 A1 | | 6/2008 | Van Hoist et al. |
| 2008/0183164 A1 | | 7/2008 | Elkins et al. |
| 2008/0294073 A1 | | 11/2008 | Barthe et al. |
| 2008/0319517 A1 | | 12/2008 | Cumbie |
| 2010/0010480 A1 | | 1/2010 | Mehta et al. |
| 2010/0114086 A1 | | 5/2010 | Deem et al. |
| 2010/0211059 A1 | | 8/2010 | Deem et al. |
| 2012/0203218 A1* | | 8/2012 | Bonn ................. A61B 18/1815 |
| | | | 606/33 |
| 2013/0190750 A1* | | 7/2013 | Behnke, II ......... A61B 18/1815 |
| | | | 606/33 |
| 2013/0282084 A1 | | 10/2013 | Mathur et al. |
| 2014/0066837 A1 | | 3/2014 | Moy |
| 2016/0324577 A1 | | 11/2016 | Beale et al. |
| 2018/0036551 A1 | | 2/2018 | McErlean et al. |
| 2018/0280715 A1 | | 10/2018 | McErlean et al. |
| 2019/0255348 A1 | | 8/2019 | Beale et al. |
| 2019/0274758 A1 | | 9/2019 | Beale et al. |
| 2020/0353278 A1 | | 11/2020 | McErlean et al. |

FOREIGN PATENT DOCUMENTS

| | | |
|---|---|---|
| WO | WO 91/03207 | 3/1991 |
| WO | WO 93/22977 | 11/1993 |
| WO | WO 98/49933 | 11/1998 |

OTHER PUBLICATIONS

Search Report for United Kingdom Patent Application No. GB1515426.3, dated Jan. 28, 2016, 1 page.

Official Action for United Kingdom Patent Application No. GB1515426.3, dated Apr. 24, 2020, 4 pages.

"Phenol," HPA Compendium of Chemical Hazards, 2011, Version 4, 32 pages.

Bevans et al. "A comparison of electrosurgery and sharp debridement in the treatment of chronic neurovascular, neurofibrous and hard corns. A pragmatic randomised controlled trial," The Foot, Mar. 2010, vol. 20, No. 1, pp. 12-17.

Cavaliere "Treatment of Porokeratosis Plantaris Discreta," The Podiatry Institute, (Predilection and Clinical Assessment), 1993, pp. 145-149 [retrieved online from: www.poodiatryinstitute.com/pdfs/update_1993/1993_28.pdf].

Chapeskie, "Ingrown Toenail or overgrown toe skin?" Canadian Family Physician, 2008, vol. 54, No. 11, pp. 1561-1562.

Choi et al. "Short-Term Heat Exposure Inhibits Inflammation by Abrogating Recruitment of and Nuclear Factor-κB Activation in Neutrophils Exposed to Chemotactic Cytokines." The American Journal of Pathology, 2008, vol. 172(2), pp. 367-377.

Clayton et al., Patty's Industrial Hygiene and Toxicology, 3rd Edition, J Wiley and Sons, New York, 1982, p. 2583.

Coughlin "Common Causes of Pain in the Forefoot in Adults," The Journal of Bone & Joint Surgery (Br), Aug. 2000, vol. 82-B, No. 6, pp. 781-790.

De Pomerai et al. "Growth and maturation of the nematode Caenorhabditis elegans following exposure to weak microwave fields." Enzyme and Microbial Technology, 2002, vol. 30(1), pp. 73-79.

Fausch et al. "Human Papillomavirus Can Escape Immune Recognition through Langerhans Cell Phosphoinositide 3-Kinase Activation." The Journal of Immunology, 2005, vol. 174(11), pp. 7172-7178.

Gao et al. "Non-ablative controlled local hyperthermia for common warts." Chinese Medical Journal, 2009, vol. 122(17), pp. 2061-2063.

Hong-Xia et al. "Detection with the Polymerase Chain Reaction of Human Papillomavirus DNA in Condylomata Acuminata Treated with CO2 Laser and Microwave," International Journal of Dermatology, Mar. 1995, vol. 34, No. 3, pp. 209-211.

Kashima et al. "Polymerase chain reaction identification of human papillomavirus DNA in CO2 laser plume from recurrent respiratory papillomatosis." Otolaryngology Head Neck Surgery, 1991, vol. 104(2), pp. 191-195.

Koltaj "Er:YAG Laser Treatment of Intractable Plantar Keratosis (IPK)," Journal of the Laser and Health Academy, May 2013, vol. 2013, No. 1, pp. 32-35 [retrieved online from: https://www.laserandhealthacademy.com/media/objave/academy/priponke/32_35 koltaj___intractable_plantar_keratosis___jlaha_2013_1.pdf].

Li et al. "Detection with the Polymerase Chain Reaction of Human Papillomavirus DNA in Condylomata Acuminata Treated with CO2 laser and Microwave." International Journal of Dermatology, 1995, vol. 34(3), pp. 209-211.

Lipke "An Armamentarium of Wart Treatments," Clinical Medicine & Research, 2006, vol. 4(4), pp. 273-293.

Ogura et al. " Microwave hyperthermia treatment increases heat shock proteins in human skeletal muscle," British Journal of Sports Medicine, 2007, vol. 41, pp. 453-455.

Skitzki et al. "Hyperthermia as an immunotherapy strategy for cancer." Current Opinion in Investigational Drugs, Jun. 2009, vol. 10(6), pp. 550-558.

Smith et al. "Microwave thermal balloon angioplasty in the normal rabbit," American Heart Journal, Jun. 1992, vol. 123, No. 6, pp. 1516-1521.

Tonomura et al. "Effects of Heat Stimulation via Microwave Applicator on Cartilage Matrix Gene and HSP70 Expression in the Rabbit Knee Joint." Journal of Orthopaedic Research, 2008, vol. 26(1), pp. 34-41.

* cited by examiner

INTERFERENCE SUPPRESSION APPARATUS AND METHOD

CROSS-REFERENCE TO RELATED APPLICATIONS

This application claims the benefit of United Kingdom Application No. 1515426.3 filed 31 Aug. 2015, the entire contents of which are incorporated herein by reference.

FIELD

The present invention relates to a method of suppression of electromagnetic interference (EMI) from a medical microwave delivery system, for example a medical microwave delivery system used in the ablation of biological tissues, and an apparatus in which such a method of suppression is implemented.

BACKGROUND

Medical microwave systems may be used in the ablation of biological tissues. In a medical microwave system that is used for ablation, microwave energy may be delivered from an microwave energy generator, via a connecting cable, to a radiating applicator that transfers the microwave energy into the tissue. The radiating applicator may comprise a radiating element. The radiating element may be placed in contact with biological tissue of a patient, or surrounded by such tissue, or placed at a small distance from such tissue.

EN 60601 Medical Electrical Equipment and Systems is a European standard which defines a set of requirements for medical electrical equipment. Collateral standards such as IEC 60601-2-6:2012 define further requirements for microwave therapy equipment. Patient safety standards such as EN 60601 and related collateral standards may present a key design requirement for medical microwave systems, which is that the medical microwave system must be designed to ensure a sufficient level of electrical isolation between conductive and insulated patient-contacting elements and equipment earthed parts. A microwave energy generator of a medical microwave system may therefore may be isolated from the mains supply and chassis earth path of the medical microwave system by means of an isolation barrier, to prevent contact with an earthed housing. The isolation barrier may comprise, for example, a medical grade isolating transformer and/or dielectric standoffs.

Various electromagnetic compatibility (EMC) regulations define requirements for microwave equipment, for example European standard EN55011 and FCC regulations for industrial, scientific and medical (ISM) equipment and radiated emissions. Electromagnetic compatibility regulations (IEC 60601-1-2:2014) set limits on electromagnetic radiation emission and immunity.

A further key design requirement for medical microwave equipment is the control of undesired electromagnetic radiation emission, such that electromagnetic interference (EMI) is not caused to nearby electronic equipment and such that the medical microwave equipment is compliant with electromagnetic compatibility regulations. Emission of unwanted electromagnetic radiation that may be capable of causing electromagnetic interference may be referred to as EMI emission or EMI interference.

In some circumstances, undesired electromagnetic radiation emission may occur at a frequency different from frequencies of the fundamental delivery band (the band in which the medical microwave equipment is intended to deliver microwave energy). For example, in an exemplary system the fundamental delivery band may be 1 to 10 GHz but unwanted electromagnetic radiation emissions may manifest at other radio frequencies, for example in the 100 MHz to 300 MHz range.

A combination of a requirement for electrical isolation and the requirement for the control of undesired electromagnetic radiation emission poses a challenge to system designers. In a medical device the chassis ground must be isolated from the patient for safety. This means that conductive patient contacting parts have to be electrically isolated from the chassis ground.

A connecting cable may be electrically isolated from the chassis ground (or electrical earth) to create an isolated ground (0V). This is commonly referred to as a floating ground. For example in Type B floating medical devices (classified as Type BF) a coaxial cable ground may be at a different electrical potential to the chassis ground. Spurious emissions from internal circuitry and internal wiring that may normally (for example, in a fully grounded system) be contained within the enclosure of the medical microwave system may induce currents on floating transmission paths. Any cable that is connected to the floating parts may carry off such induced currents and can act as an unintended antenna as it emerges from the system ground plane, creating unwanted radiation emission.

In many prior art examples, DC blocking elements are utilised to provide patient isolation. Interference in these systems is filtered using combinations of resistive and capacitive elements connected to the chassis ground prior to the DC blocking components thus maintaining isolation between the patient and the chassis ground and eliminating the transmission of electromagnetic interference.

Filtering schemes may not be able to be applied to a floating circuit directly (without DC blocking) as they may create a path to the chassis ground that may exceed the allowable leakage current limits in the 60601 standard. Additionally, filtering schemes may be overcome by high potential voltages (1.5 KV+) between the chassis and the applied part. Medical devices must withstand such high potential voltages for patient safety. Often improvements in filters made to withstand high potential testing, such as increased capacitance, have the effect of creating more leakage current.

As the robust filtering schemes used in the known prior art deal with interference prior to the DC blocking elements, there may be no requirement in such prior art devices for any additional schemes such as the one described herein.

For example, US 2013/0190750 employs a DC blocking and filtering scheme to isolate the EMC path in a medical device. A coaxial cable is connected to a microwave energy source by an isolation circuit having capacitive values such that the isolation circuit has a low impedance at a fundamental frequency of the microwave energy source, and a high impedance at lower frequencies. A parallel plate capacitor is formed by a ground reference shield connected to a ground of the device (for example, a chassis earth) and a patient reference shield connected to a floating ground.

The use of specific DC blocking elements however may reduce the available output power of the system as the DC blocking elements may create a path loss that attenuates some of the transmitted power. For example, components such as the Huber and Suhner broadband DC block (H&S part #9077.17.0015) has an insertion loss of 0.5 dB which is will reduce the power transmitted by 9%.

In the prior art there are also examples where sensitive receiver circuits are protected from receiving external interference using ferrites.

U.S. Pat. No. 4,757,825 describes a cardiopulmonary monitor comprising a transducer. A lower conductive layer of the transducer is connected to an earth ground through a ferrite bead and an active electrical layer of the transducer is connected to an amplifier through another ferrite bead. The use of the ferrite beads may stop interference in the form of AM and FM radio signals being received by the transducer.

EP 0267403 relates to a capacitive partition member for galvanic separation of a coaxial cable, where the coaxial cable is for use in broadband communication systems. U.S. Pat. No. 7,052,283 describes a sheath current attenuator for a coaxial cable, which is used to screen interference from a TV signal. Neither EP 0267403 nor U.S. Pat. No. 2,052,283 relates to a medical system.

SUMMARY

In an aspect of the invention, there is provided a medical microwave delivery system, comprising a microwave generator for providing microwave energy, wherein the microwave generator is electrically isolated from an electrical earth of the medical microwave delivery system, a cable configured to transfer microwave energy from the microwave generator, and a radiation suppression element configured to at least partially surround at least part of the cable. The cable may comprise a coaxial cable. The radiation suppression element may comprise a ferrite element. The radiation suppression element may comprise a magnetic core. The magnetic core may comprise a ferrite core.

In known medical microwave delivery systems, when a cable is connected to a microwave generator that is isolated from electrical earth (floating) to meet patient isolation standards, unwanted currents may be generated on the cable, and the cable may act as an antenna and transmit unwanted radiation. Such unwanted radiation may interfere with other electrical equipment. By providing a ferrite element around the floating cable, the unwanted currents, and therefore the unwanted emissions, may be suppressed. In some circumstances, the unwanted currents may be suppressed without introducing DC blocking elements which may reduce the output power.

The system may be for use in ablation of biological tissue. The microwave generator may be isolated from the electrical earth by a medical grade isolating transformer. The microwave generator may be isolated from the electrical earth by dielectric elements, for example dielectric standoffs. The system may meet electrical interference requirements, for example EMC regulations, and medical electrical isolation requirements.

The ferrite element may be configured to suppress emission of electromagnetic radiation from the coaxial cable. The ferrite element may be configured to suppress the emission of electromagnetic radiation within a desired suppression band of frequencies. The emission of electromagnetic radiation may be suppressed such that an electric field strength of the electromagnetic radiation is below a threshold value. The electric field strength may be a quasi-peak value for electric field strength. The threshold value may be 50 dBμV/m.

The desired suppression band may be between 10 MHz and 500 MHz. The desired suppression band may be between 100 MHz and 200 MHz. The desired suppression band may be between 100 MHz and 300 MHz. A band between 100 MHz and 300 MHz may be the optimal range of performance for ferrites. However, material may be chosen to operate in other bands such as 25 MHz to 1 GHz depending upon the performance characteristics of the ferrite material selected. At least one frequency within the desired suppression band may be different from a frequency of the microwave energy generated by the microwave generator.

A frequency of the microwave energy generated by the microwave generator may be a frequency between 1 GHz and 10 GHz. The microwave generator may generate microwave energy having frequencies between 1 GHz and 10 GHz. The microwave generator may generate microwave energy having frequencies between 5 GHz and 15 GHz. The microwave generator may generate microwave energy having frequencies between 300 MHz and 2.5 GHz.

In practice the microwave generator may operate within an ISM (Industrial, Scientific and Medical) frequency such as between 2.4 GHz and 2.5 GHz or at 5.8 GHz or 915 MHz. The microwave generator may operate at a frequency between 902 MHz and 928 MHz. The microwave generator may operate at a frequency between 5.725 GHz and 5.875 GHz. The microwave generator may generate microwave energy at a single frequency and/or microwave energy across a range of frequencies.

A geometry and/or a material of the ferrite element may be selected to provide suppression of electromagnetic radiation within the desired suppression band. A size and/or shape of the ferrite element may be selected. A size of an aperture in the ferrite core may be selected, wherein the connecting cable passes through the aperture.

The coaxial cable may pass through the ferrite element two or more times. By passing the coaxial cable through the ferrite element more than once, increased suppression may be achieved. The coaxial cable may be passed through the ferrite element three, four, five or more times. Each additional pass may result in additional suppression.

The ferrite element may comprise a ferromagnetic material that provides an electrical impedance. The ferrite element may be configured such that, in use, the electrical impedance attenuates high-frequency electromagnetic currents carried by the coaxial cable. By attenuating the high-frequency electromagnetic currents carried by the coaxial cable, a level of unwanted radiation from the cable may be reduced.

The system may further comprise a housing connected to the electrical earth. The microwave generator may be housed in the housing. The system may further comprise dielectric elements, for example dielectric standoffs, between the microwave generator and the housing. The ferrite element may at least partially surround a part of the cable that is inside the housing. The ferrite element may at least partially surround a part of the cable that is outside the housing.

The system may further comprise a mains power supply. The mains power supply may be connected to a mains earth. The electrical earth from which the microwave generator is isolated may be, or may be connected to, the mains earth.

The coaxial cable may be configured to transfer microwave energy from the microwave generator to a microwave delivery device. The microwave delivery device may be outside the housing. The microwave delivery device may comprise a microwave applicator. The microwave applicator may be configured to transfer microwave energy to tissue of a patient.

The coaxial cable may comprise an insulated coaxial cable. The coaxial cable may be encapsulated in an insulating jacket such as FEP (fluorinated ethylene propylene) or PTFE (polytetrafluoroethylene). An insulated coaxial cable may provide enhanced suppression as each turn of the cable through the ferrite may be isolated from the other turns of the cable. The coaxial cable may comprise an inner conductor and outer conductor. In use, the outer conductor may be at a floating ground potential and the inner conductor may be at a positive or negative supply voltage, alternating potential or other potential operating at radio frequency or microwave frequency from DC to 300 GHz.

The ferrite element may comprise a ferrite core. The ferrite element may comprise a ferrite bead, filter or choke. The ferrite element may be a continuous ring or toroid or may be split to enable it to be combined to form this.

The ferrite core may comprise a ferromagnetic or ferrimagnetic material. At least one further ferrite element may surround another at least part of the connecting cable. The medical microwave delivery system may comprise at least one further cable, at least part of which is at least partially surrounded by a further ferrite element.

The ferrite element may comprise a solid form with an internal through hole through which the coaxial cable is passed.

The ferrite element may comprise at least two parts configured to be fitted around the coaxial cable such as to, in combination, at least partially surround the at least part of the coaxial cable.

In a further aspect of the invention, which may be provided independently, there is provided a method for suppressing emission of electromagnetic radiation in a medical microwave delivery system, the medical microwave delivery system comprising a microwave generator for providing microwave energy, wherein the microwave generator is electrically isolated from an electrical earth of the medical microwave delivery system and a coaxial cable configured to transfer microwave energy from the microwave generator, wherein the method for suppressing emission comprises fitting a radiation suppression element such that the radiation suppression element at least partially surrounds at least part of the cable. The cable may comprise a coaxial cable. The radiation suppression element may comprise a ferrite element. The radiation suppression element may comprise a magnetic core. The magnetic core may comprise a ferrite core. The electrical earth from which the microwave generator is isolated may be an electrical chassis earth.

In a further aspect of the invention, which may be provided independently, there is provided a coaxial cable arrangement comprising a coaxial cable configured to transfer microwave energy from a microwave generator, and a ferrite element that at least partially surrounds at least part of the coaxial cable.

In a further aspect of the invention, which may be provided independently, there is provided an electromagnetic interference and radiation suppression system for a medical microwave energy delivery system, comprising the fitment of a ferrite core around a coaxial connecting cable which is connected to a microwave generator system that is electrically isolated from the equipment earthing path by means of a medical grade isolating transformer.

The ferrite core geometry and materials may be selected to provide a suitable impedance across the desired frequency band for which suppression of EMI is required.

The ferrite core may be manifested as a solid form with an internal through hole, for example but not limited to a cylindrical form with a hole along its central axis through which the cable may be inserted.

The ferrite core may be a split-form ferrite core. The split-form ferrite core may be housed within a casing which provides a mechanism for a snap or clamp fitment over the coaxial connecting cable. The casing may be, for example but not limited to, a plastic casing.

Any feature in one aspect of the invention may be applied to other aspects of the invention, in any appropriate combination. For example, apparatus features may be applied to method features and vice versa.

DETAILED DESCRIPTION

Figure 1:
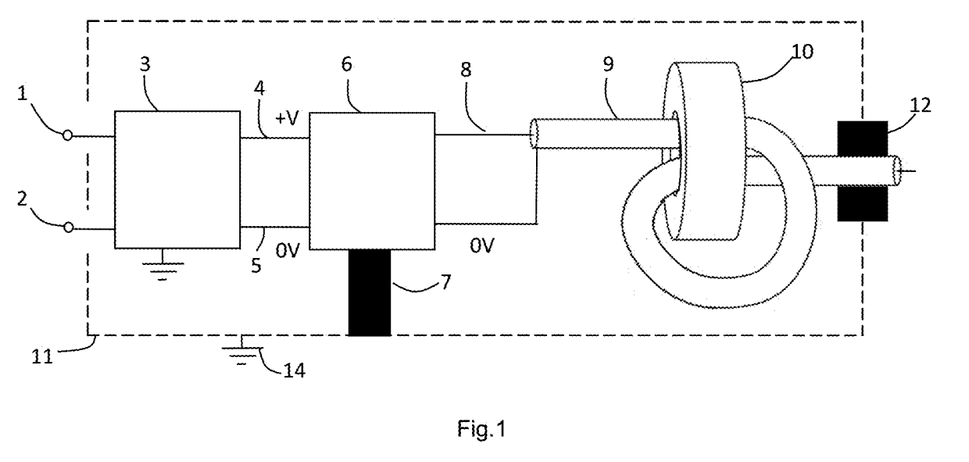
FIG. 1 is an electrical schematic illustration of a medical microwave energy delivery system in accordance with an embodiment.

A system for delivering medical microwave energy according to an embodiment is illustrated in FIG. 1. The system comprises a microwave generator 6 which supplies microwave energy to a microwave applicator (not shown) via a connecting cable 9. In the present embodiment, the connecting cable 9 is an insulated coaxial connecting cable. The microwave generator 6 comprises microwave supply circuitry.

In use, the microwave generator 6 generates microwave energy of a desired frequency or frequencies (for example, a frequency or frequencies between 1 and 10 GHz) and the microwave applicator is used to deliver the microwave energy to biological tissue of a patient. In the present embodiment, the microwave applicator is used to perform ablation of biological tissue. In other embodiments, the microwave applicator may be used to supply microwave energy for other medical purposes.

A mains supply 1, 2 supplies mains power to the microwave generator 6. The mains supply 1, 2 is isolated from the microwave generator 6 by a medical grade isolation transformer 3. The live and neutral of the mains supply are indicated by 1 and 2 respectively. The mains supply 1 and 2 represent the live and neutral from the wall supply, for example from a wall outlet.

In the present embodiment, the medical grade isolation transformer 3 comprises an AC/DC converter to provide a system positive voltage supply 4 and a system ground 5, which may also be referred to as a 0V reference, system 0V ground or floating ground. The voltage supply 4 and system ground 5 power the microwave generator 6. In further embodiments, the medical grade isolation transformer 3 may comprise an AC/DC converter, transformer or power supply unit. The medical grade power supply 3 takes the mains as an input and creates an isolated DC output.

The microwave generator 6 is enclosed within an earthed enclosure 11. The earthed enclosure may be referred to as a chassis or housing. The earthed enclosure 11 is connected to chassis earth 14, which may also be referred to as an enclosure earth.

The microwave generator 6 is electrically isolated from an equipment earthing path of the microwave energy delivery system by the medical grade isolating transformer 3. The microwave generator 6 is supported on insulating dielectric supports 7 which electrically isolate the microwave generator 6 from the earthed enclosure 11. The insulating dielectric supports 7 are dielectric insulators. The insulating dielectric supports 7 provide mechanical support between the microwave generator 6 and the grounded chassis 11.

In medical applications requiring electrically floating connectors, such as the microwave delivery system shown in FIG. 1, the chassis earth 14 and system ground or 0V reference 5 may be at different potentials due to the isolation of the microwave generator 6 from the earthed enclosure 11, which is due to the requirement to isolate the patient from the earth 14 to prevent the risk of electrical shock.

The difference in potential between the chassis earth 14 and the system ground 5 may result in an alternating voltage potential. In known microwave delivery systems, when the microwave generator 6 is connected to conductive cabling, particularly to long lengths of conductive cabling, the conductive cabling may act as an antenna and may transmit and/or receive system noise in the form of EMI interference.

The microwave generator output 8 is connected to supply the fundamental frequency or frequency band to the microwave connecting cable 9. The microwave generator 6 enclosure is separated from the chassis 11 by insulating dielectric supports 7. The fundamental frequency or frequency band may be the frequency or frequency band in which the medical microwave delivery system is intended to deliver microwave energy. For example, the medical microwave delivery system may be intended to deliver frequencies between 1 GHz and 10 GHz.

The microwave generator 6 is electrically isolated (floated) from the chassis ground 14 and is powered by the mains supply 1, 2 and the medical grade isolation transformer 3 (which in the present embodiment is a type BF medical grade isolating power supply e.g. Craftec GNT400 or equivalent) to provide the required patient isolation, negating the requirement for a full coaxial microwave DC block.

A full coaxial DC block may be any component or method that inserts a capacitive path in line with the outer shield and also in line with the inner centre conductor. In the present embodiment, the PSU 3 negates the requirement for a full coaxial DC block since the isolations are built in. Beyond the PSU 3, everything has to float with respect to the chassis ground to maintain isolation. Hence there may be issues with EMI as floating circuits may radiate quite easily.

In the present embodiment, the microwave connecting cable 9 is a single length of coaxial cable extending to the intended recipient device or target (in this embodiment, to the microwave applicator). On passing through the enclosure 11, the connecting cable 9 is isolated from the enclosure by dielectric insulators 12. Dielectric insulators 12 may provide mechanical support to the grounded chassis.

In an alternative embodiment, a first microwave connecting cable 9 extends within the chassis enclosure 11 to an insulated panel-mounted microwave coaxial connector or adapter arrangement such as an SMP, BMA or SMA connector supplied by Amphenol or M/A-Com. The panel-mounted microwave coaxial connector or adapter arrangement is mounted to a surface which is insulated from the chassis enclosure 11. A second microwave connecting cable is connected to the panel-mounted microwave coaxial connector or adapter arrangement externally to the enclosure 11. The second microwave connecting cable extends to the intended recipient device or target, for example to a microwave applicator.

A ferrite core 10 is fitted around the outside of the microwave connecting cable 9 that connects the microwave generator 6 to the intended recipient device or target. In the embodiment of FIG. 1, the ferrite core 10 is fitted to a part of the connecting cable 9 that is inside the enclosure 11. In other embodiments, the ferrite core 10 may be fitted to a part of the connecting cable 9 that is external to the enclosure 11. The ferrite core 10 may be fitted around the external of the microwave cable which connects the microwave generator 6 to the applicator. The ferrite core may be fitted around the cable at any suitable position. In other embodiments, any element that provides radiation suppression may be used, for example any appropriate magnetic core.

In the present embodiment, the connecting cable 9 is looped through the ferrite core 10 such that it passes twice through a hole in the ferrite core 10.

The ferrite core 10 is manufactured from a ferromagnetic or ferrimagnetic material which provides an electrical impedance that attenuates high-frequency electromagnetic currents carried by the coaxial connecting cable 9, thereby reducing radiated signal levels from the cable to a level that may be acceptable to meet EMC requirements.

The ferrite core 10 acts as an inductor to form a passive low-pass filter, which results in an impedance for high-frequency signals. The ferrite core 10 attenuates high frequency EMI/RFI (radio frequency interference) electronic noise. The energy of high-frequency signals may be reflected back by the cable, or may be dissipated as low level heat.

The consequent attenuation of unwanted high-frequency electrical currents may result in a lowering of the transmitted power level of unwanted emissions and/or received power level of unwanted emissions from any electrically-connecting cable that is acting as an unintended radiating antenna, or that would act as an unintended radiating antenna were it not for the presence of the ferrite core 10.

Spurious radiation created by the floating circuit is absorbed before it can be radiated. This approach for a floating circuit in a medical device is different from the prior art cited above in which a ferrite is used to protect a sensitive receiver circuit from receiving external interference.

The profile (impedance vs. frequency) and materials of the ferrite core 10 may be carefully chosen to present a desired electrical impedance within a desired frequency band over which suppression of emissions is required. The desired frequency band may be, for example, a frequency band in the range from 100 MHz to 1000 MHz. The impedance at a desired frequency band may be increased by increasing the number of insulated turns of each conductor that passes through the ferrite. For example, a Wurth Elektronik 7427154 Ferrite 16 mm Core has a maximum impedance of 900 Ohm at 800 MHz for one conductor turn around the ferrite. With two turns the maximum impedance can be lowered to 300 MHz.

The ferrite core geometry and/or ferrite core materials may be selected to provide suitable impedance. For example, the size and/or shape of the ferrite core 10 may be selected. A material of which the ferrite core 10 is made may be selected. The geometry and/or materials required may depend on the size and characteristics of the connecting cable 9 and/or on the frequency of magnetic energy that is being delivered by the cable. A size of an aperture in the ferrite core 10 may be selected, for example to allow for a specified number of cable loops and/or minimize air gap between the cable and the ferrite.

In the embodiment shown in FIG. 1, the connecting cable 9 is looped through the ferrite core 10 to ensure the cable passes through twice. In further embodiments, the connecting cable 9 may be looped through the ferrite core 10 one or more additional times. The additional loops may further increase the electrical impedance provided by the ferrite core 10 and/or lower the frequency of the maximum impedance. The additional loops may thereby provide even greater suppression to unwanted radiated emissions.

The connecting cable 9 may pass once through a ferrite core 10, or multiple times through the same ferrite core 10. In some embodiments, the connecting cable 9 may pass through more than one ferrite core 10. Any suitable ferrite element or elements may be used.

In the embodiment of FIG. 1, the ferrite core 10 comprises a solid cylinder comprising ferrite material, with a hole through which the connecting cable 9 may be inserted. The hole is an internal through hole extending along a central axis of the ferrite core 10. In other embodiments, any suitable solid form may be used through which the connecting cable 9 can be passed one or more times.

The number of times that the cable is passed through the ferrite may depend on the frequency at which the ferrite is required to work best. If there are too many loops, the ferrite may operate at too low a frequency and may not attenuate adequately at the required frequency. In some cases, the roll off in attenuation may be quite fast. In some cases, at 600 to 700 MHz beyond the peak, the ferrite may become ineffective.

In alternative embodiments, the ferrite core 10 may be configured as a snap-on or clamp-on device (for example, a Wurth Elektronik 74271132 Ferrite Core). The snap-on or clamp-on device may comprise two or more ferrite parts contained within a housing. The housing may be made of a plastic material. The housing may be referred to as a casing. The casing may provide a mechanism for a snap or clamp fitment over the connecting cable 9.

A snap-on device may be a device formed of two or more ferrite parts and a snap cover that snaps together to hold the ferrite parts together around the coaxial cable. A clamp-on device may be a device formed of two or more ferrite parts and a mechanism for clamping the ferrite parts together around the coaxial cable.

In embodiments in which the ferrite core 10 is a solid form, the connecting cable 9 may need to be passed through the ferrite core 10 before the connecting cable 9 is connected to other parts of the microwave energy delivery system, for example to microwave generator 6 or to an external connector. In the snap-on or clamp-on embodiment, the ferrite core 10 may be fitted into the microwave energy delivery system at a later stage of manufacturing when all cable connections have been completed. The ferrite core 10 may be placed around the connecting cable 9 after the connecting cable 9 has been connected to other parts of the microwave energy delivery system, for example the microwave generator 6.

The system of FIG. 1 may provide suppression of EMI within a medical microwave generator system whilst maintaining patient safety requirements for electrical isolation. An isolated (plastic coated) ferrite core is incorporated into an electrically isolated system. In some circumstances, the electrical isolation performance of the system may be unchanged by the addition of a non-insulated ferrite core 10 if it is positioned with sufficient clearance from grounded (chassis ground) conductors, since no modifications are made to any floating or system ground configurations by the addition of the ferrite core 10.

Figure 2:
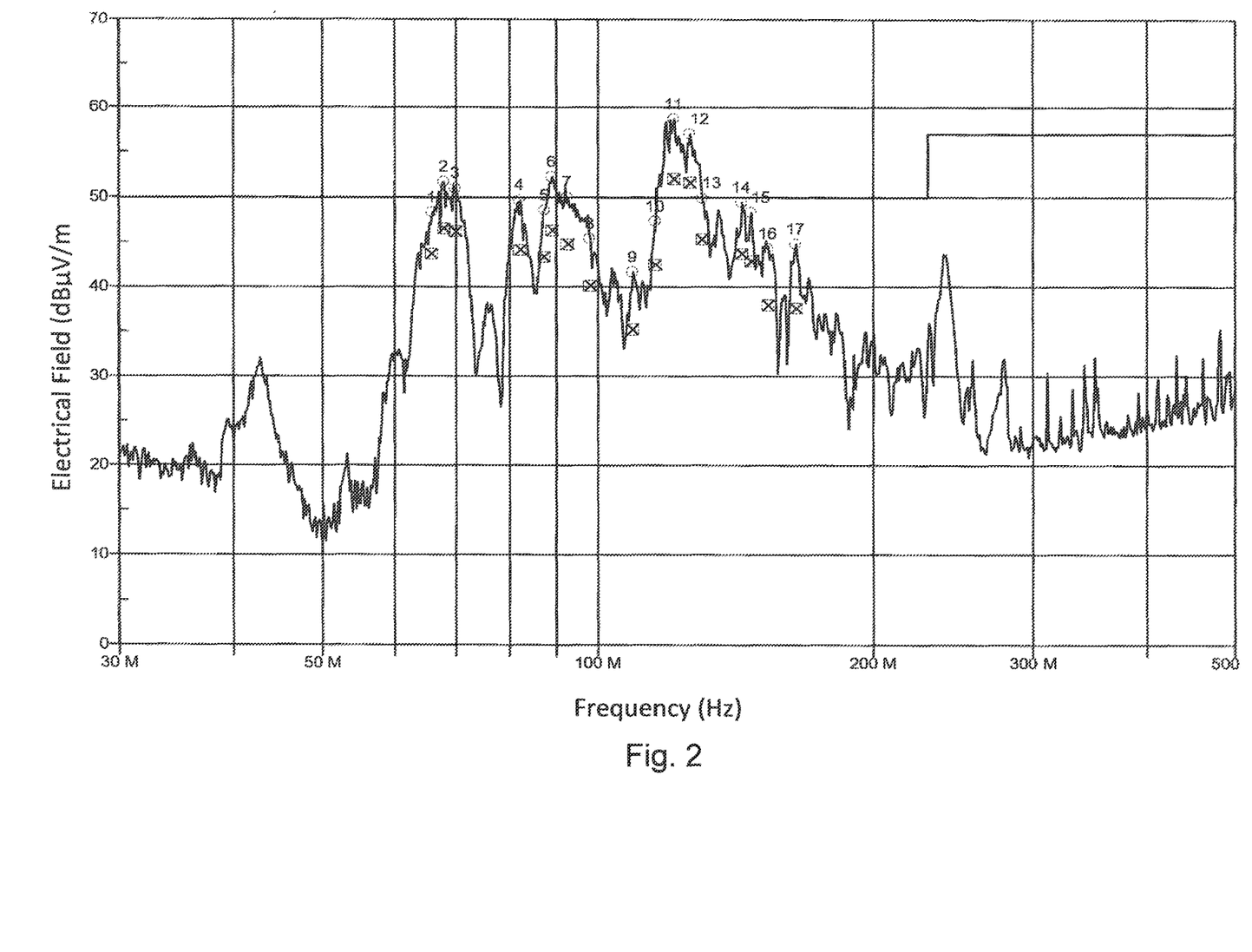
FIG. 2 is a plot of emissions for a medical microwave delivery system without ferrite on the coaxial output.

FIG. 2 shows a plot of results for EMI analysis of a microwave energy delivery system with floating output circuits. The microwave energy delivery system of FIG. 2 does not comprise a ferrite core 10 or cable loop as illustrated in FIG. 1.

In the results presented in FIG. 2, electrical field in dBµV/m is plotted against frequency in Hz over a range from 30 MHz to 500 MHz. Peak and quasi-peak results are measured and the results plotted on the graph of FIG. 2. Quasi-peak results are indicated by crossed boxes.

The EN55011 class A limit requires emissions having quasi-peak values below 50 dBµV/m in the frequency range of 100 MHz to 200 MHz. In FIG. 2, some quasi-peak EMI emission levels are present that have values above the 50 dBµV/m limits stipulated by the EN55011 class A limit between the frequency range of 100 to 200 MHz, which would prevent the device achieving compliance with the EN55011 standard.

Figure 3:
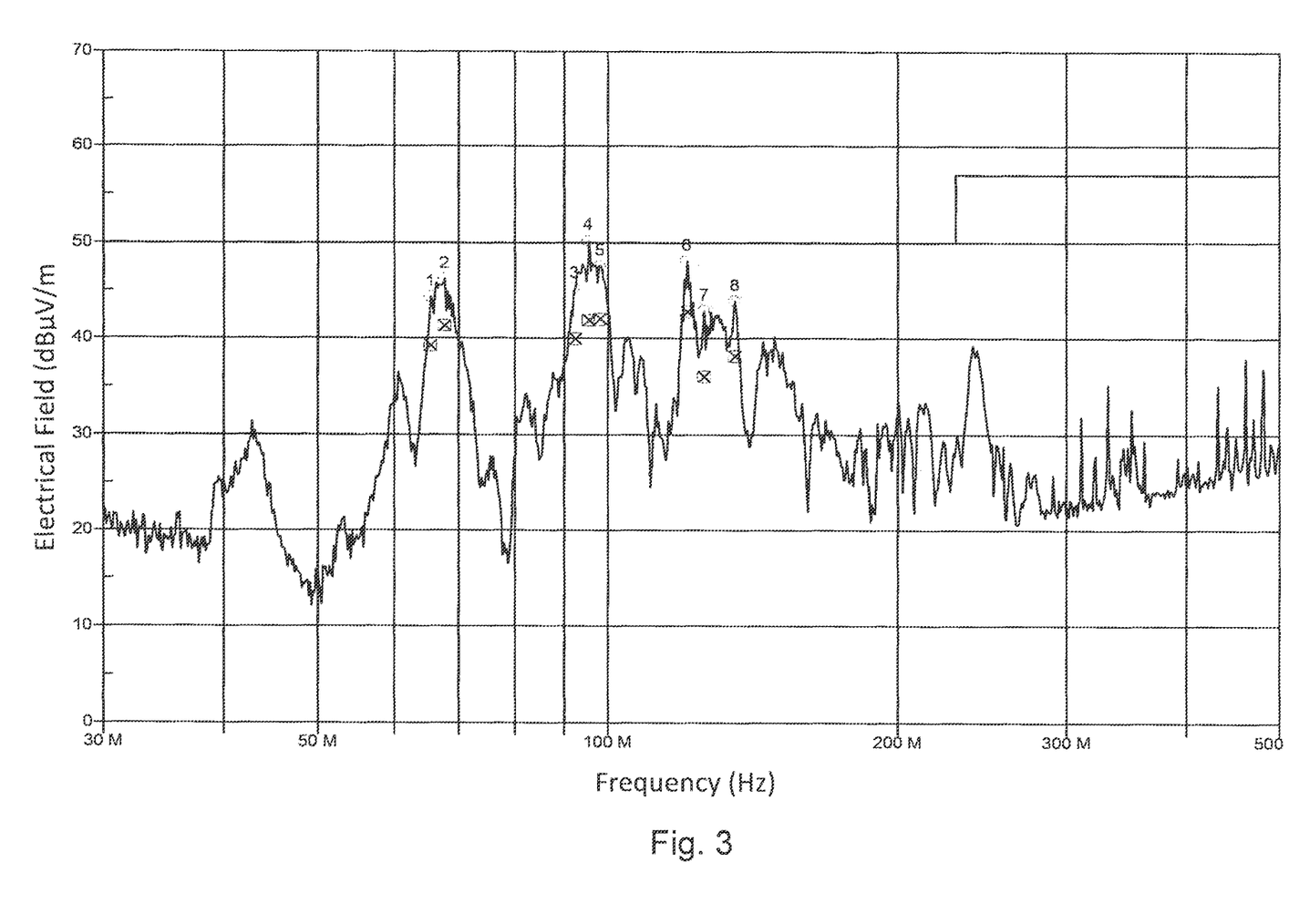
FIG. 3 is a plot of emissions for a medical microwave delivery system with ferrite on the coaxial output.

FIG. 3 illustrates the results of EMI analysis for an embodiment of a microwave energy delivery system having a ferrite core 10 and cable loop as illustrated in FIG. 1, but otherwise the same as the microwave energy delivery system for which the results of FIG. 2 were obtained.

In the results of FIG. 3, quasi-peak (indicated by crossed boxes) EMI emissions are not present above the limits stipulated by EN55011 class A limit for 100 to 200 MHz. The presence of the ferrite core 10 and cable loop may therefore permit the device to achieve compliance with the EN55011 standard.

Figure 4:
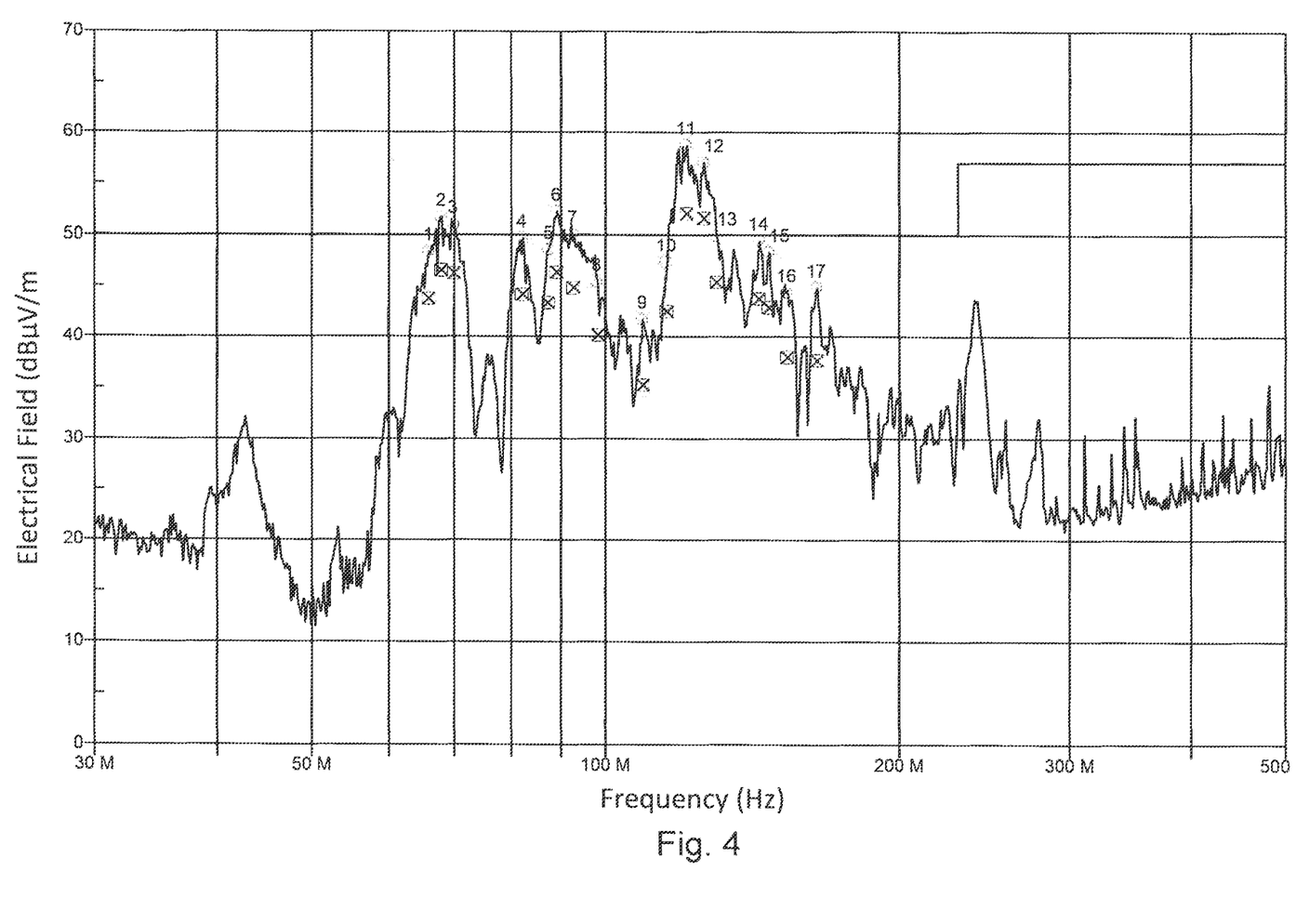
FIG. 4 is an overlay of FIGS. 2 and 3.

In FIG. 4, the results of FIG. 2 (line 20) and FIG. 3 (line 22) are overlaid for comparison. A required emissions level (quasi-peak of 50.5 dBµV/m up to 230 MHz, 57.5 dBµV/m over 230 to 500 MHz) is indicated by dotted line 24 in FIG. 4.

The emissions limits are defined in CISPR 22:2006 and EN55022:2006. For 30 MHz-230 MHz, the limits are 40 dBµV/m at 10 m and 50.5 dBµV/m at 3 m. For 230 MHz-1000 MHz, the limits are 47 dBµV/m at 10 m and 57.5 dBµV/m at 3 m). In the example of FIG. 4, no emissions were present above 500 MHz and the graph was truncated for legibility.

In the embodiment described above with reference to FIG. 1, the connecting cable 9 is an insulated coaxial cable. In other embodiments, an uninsulated coaxial cable may be used. However, an uninsulated coaxial cable may not benefit from the additional attenuation that may be obtained by using insulated windings applied around the ferrite core 10. In addition, the use of an uninsulated coaxial output may be less likely to withstand HI-POT (high voltage) testing as a conductive path via the ferrite core 10 may exist.

It will be understood that the present invention has been described above purely by way of example, and that modifications of detail can be made within the scope of the invention.

Each feature disclosed in the description and (where appropriate) the claims and drawings may be provided independently or in any appropriate combination.

The invention claimed is:

1. A medical microwave delivery system, comprising:
   a microwave generator for providing microwave energy, wherein the microwave generator is electrically isolated from an electrical earth of the medical microwave delivery system;
   a housing connected to the electrical earth, wherein the microwave generator is housed in the housing;
   a coaxial cable configured to transfer the microwave energy from the microwave generator, wherein the coaxial cable passes through a wall of the housing and is isolated from the housing by a dielectric insulator; and
   a ferrite element configured to at least partially surround at least part of the coaxial cable that is inside the housing.

2. The system according to claim 1, wherein the medical microwave delivery system is configured to ablate biological tissue.

3. The system according to claim 1, wherein the microwave generator is isolated from the electrical earth by a medical grade isolating transformer.

4. The system according to claim 1, wherein the ferrite element is configured to suppress emission of electromagnetic radiation from the coaxial cable.

5. The system according to claim 4, wherein the ferrite element is configured to suppress the emission of electromagnetic radiation within a desired suppression band of frequencies.

6. The system according to claim 5, wherein at least one frequency within the desired suppression band is different from a frequency of the microwave energy generated by the microwave generator.

7. The system according to claim 5, wherein a geometry and/or a material of the ferrite element is selected to provide suppression of electromagnetic radiation within the desired suppression band.

8. The system according to claim 1, wherein the coaxial cable passes through the ferrite element two or more times.

9. The system according to claim 1, wherein the ferrite element comprises one or more ferromagnetic materials selected to have properties that provide an electrical impedance for attenuating high frequency electromagnetic currents carried by the coaxial cable.

10. The system according to claim 1, wherein the coaxial cable is connected to a microwave delivery device and is configured to transfer the microwave energy from the microwave generator to the microwave delivery device.

11. The system according to claim 10, wherein the microwave delivery device is outside the housing.

12. The system according to claim 11, wherein the microwave delivery device comprises a microwave applicator.

13. The system according to claim 12, wherein the microwave applicator is configured to transfer the microwave energy to tissue of a patient.

14. The system according to claim 1, wherein the coaxial cable comprises an insulating jacket.

15. The system according to claim 1, wherein the ferrite element comprises a ferrite core.

16. The system according to claim 1, wherein the ferrite element comprises a solid form with an internal through hole through which the coaxial cable is passed.

17. The system according to claim 1, wherein the ferrite element comprises at least two parts configured to be combined to form a continuous ring or toroid fitted around the coaxial cable.

18. The system according to claim 1, further comprising at least one further cable and a further ferrite element, wherein at least part of the at least one further cable is at least partially surrounded by the further ferrite element.

19. The system according to claim 1, wherein the coaxial cable is mechanically supported by the dielectric insulator as the coaxial cable passes through the wall of the housing.

20. A method for a medical microwave delivery system, the medical microwave delivery system comprising:
    a microwave generator for providing microwave energy, wherein the microwave generator is electrically isolated from an electrical earth of the medical microwave delivery system;
    a housing connected to the electrical earth, wherein the microwave generator is housed in the housing; and
    a coaxial cable configured to transfer the microwave energy from the microwave generator, wherein the coaxial cable passes through a wall of the housing and is isolated from the housing by a dielectric insulator;
    wherein the method comprises:
        fitting a ferrite element such that the ferrite element at least partially surrounds at least part of the coaxial cable that is inside the housing; and
        passing the coaxial cable through the housing so that the coaxial cable is isolated from the housing by a dielectric insulator.

\* \* \* \* \*